(12) United States Patent
Sasaki et al.

(10) Patent No.: US 9,675,243 B2
(45) Date of Patent: Jun. 13, 2017

(54) OPHTHALMIC PHOTOGRAPHING APPARATUS

(71) Applicant: NIDEK CO., LTD., Gamagori-shi, Aichi-ken (JP)

(72) Inventors: Joji Sasaki, Gamagori (JP); Masaaki Hanebuchi, Nukata-gun (JP)

(73) Assignee: NIDEK CO., LTD., Gamagori (JP)

( * ) Notice: Subject to any disclaimer, the term of this patent is extended or adjusted under 35 U.S.C. 154(b) by 30 days.

(21) Appl. No.: 14/954,204

(22) Filed: Nov. 30, 2015

(65) Prior Publication Data

US 2016/0150953 A1 Jun. 2, 2016

(30) Foreign Application Priority Data

Dec. 1, 2014 (JP) ................. 2014-243421

(51) Int. Cl.
| | |
|---|---|
| *A61B 3/14* | (2006.01) |
| *A61B 3/10* | (2006.01) |
| *G02B 13/00* | (2006.01) |
| *G02B 26/10* | (2006.01) |
| *A61B 3/12* | (2006.01) |

(52) U.S. Cl.
CPC ............ *A61B 3/102* (2013.01); *A61B 3/1025* (2013.01); *A61B 3/1225* (2013.01); *A61B 3/14* (2013.01); *G02B 13/0095* (2013.01); *G02B 26/105* (2013.01)

(58) Field of Classification Search
USPC ............................................. 351/206
See application file for complete search history.

(56) References Cited

U.S. PATENT DOCUMENTS

2012/0140238 A1 6/2012 Horn et al.

FOREIGN PATENT DOCUMENTS

JP 2014-138904 A 7/2014

*Primary Examiner* — Jack Dinh
(74) *Attorney, Agent, or Firm* — Oliff PLC

(57) ABSTRACT

An ophthalmic photographing apparatus is provided with a SLO optical system including a first optical scanner for scanning a laser beam to obtain a front image of an examinee's eye by the laser beam, a OCT optical system including a second optical scanner for scanning measurement light to obtain a tomographic image of the examinee's eye by use of interference between the measurement light and reference light, an optical path combiner for combining optical paths of the SLO optical system and the OCT optical system, an objective lens system placed between the optical path combiner and the examinee's eye, and a relay lens system placed between the second optical scanner and the optical path combiner. The second optical scanner is placed on a side closer to the relay lens system than a focal point distance of the relay lens is.

7 Claims, 2 Drawing Sheets

OPHTHALMIC PHOTOGRAPHING APPARATUS

CROSS-REFERENCE TO RELATED APPLICATIONS

This application is based upon and claims the benefit of priority from the prior Japanese Patent Application No. 2014-243421 filed on Dec. 1, 2014, the entire contents of which are incorporated herein by reference.

BACKGROUND

The present disclosure relates to an ophthalmic photographing apparatus to capture an image of an examinee's eye.

Conventionally, an optical coherence tomography (OCT) has been known as an ophthalmic photographing apparatus capable of obtaining a tomographic image of an examinee's eye (e.g., fundus, anterior segment, etc.) in non-invasive manner. The apparatus of this type is configured for example to one-dimensionally scan measurement light on a fundus to thereby obtain information of the examinee's eye in a depth direction by use of an OCT optical system.

For the foregoing apparatus, there is known a structure that a scanning laser ophthalmoscope (a SLO optical system) for obtaining a front image of an examinee's eye is combined with an OCT optical system. As a result of two-dimensional scanning a laser beam on a portion of the examinee's eye by use of the SLO optical system, the front image of the examinee's eye is obtained. Such a combined structure of the OCT optical system and the SLO optical system may share an objective lens between them (see JP-A-2014-138904 and US 2012/140238 A1).

SUMMARY

In the apparatus configured as above, for example, the SLO optical system and the OCT optical system may be mutually subjected to the limitation of their optical arrangement. Therefore, a resultant tomographic image may be affected by noise associated with driving of an optical scanner of the OCT optical system. The optical arrangement of the SLO optical system may also be complicated.

The present invention has been made to solve at least one of the above problems and has a purpose to provide an ophthalmic photographing apparatus capable of appropriately performing both photographing of a tomographic image and photographing of a front image.

One aspect of the present disclosure provides an ophthalmic photographing apparatus comprising: a SLO optical system including a first optical scanner for scanning a laser beam, the SLO optical system being configured to obtain a front image of an examinee's eye by the laser beam; a OCT optical system including a second optical scanner for scanning measurement light, the OCT optical system being configured to obtain a tomographic image of the examinee's eye by use of interference between the measurement light and reference light; an optical path combiner configured to combine an optical path of the SLO optical system and an optical path of the OCT optical system; an objective lens system placed between the optical path combiner and the examinee's eye; and a relay lens system placed between the second optical scanner and the optical path combiner, wherein the second optical scanner is placed on a side closer to the relay lens system than a focal point distance of the relay lens system is.

DETAILED DESCRIPTION OF THE EXEMPLARY EMBODIMENTS

Figure 1:
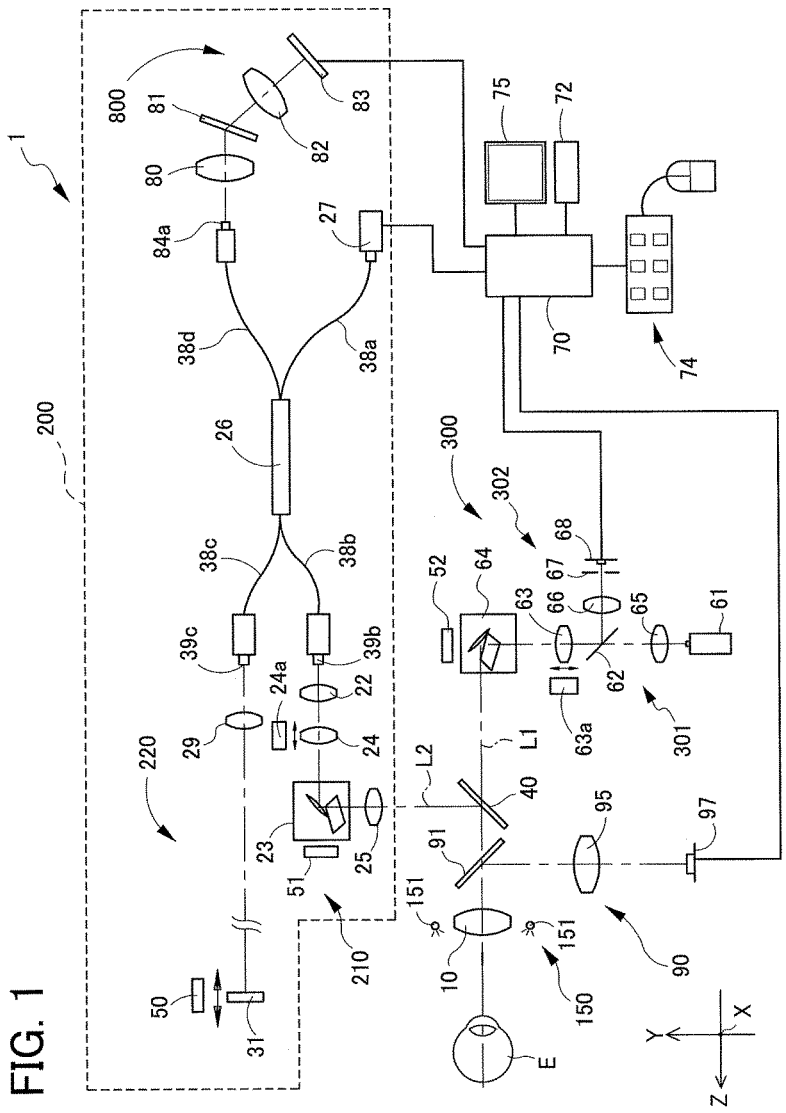
FIG. 1 is a diagram showing optical systems and a control system in an ophthalmic photographing apparatus of an embodiment.

An embodiment which is one of typical embodiments of this disclosure will be explained below referring to the accompanying drawings. Optical systems of an ophthalmic photographing apparatus 1 will be first explained referring to FIG. 1. The following explanation is made based on the premise that a depth direction of an examinee's eye E is a Z direction (a direction of an optical axis L1), a horizontal direction is an X direction, and a vertical direction is a Y direction, as shown in FIG. 1. Those optical systems are housed in a casing not shown. This casing may be moved by a known alignment moving mechanism (manually or electrically) in three dimensions with respect to the examinee's eye E.

As shown in FIG. 1, the ophthalmic photographing apparatus 1 of the present disclosure is mainly provided with an interference optical system 200 (hereinafter, referred to as an "OCT optical system") and a scanning laser ophthalmoscope optical system 300 (also referred to as a confocal optical system, which is hereinafter referred to as an "SLO optical system"). In the present embodiment, the OCT optical system 200 is utilized to obtain a tomographic image of a predetermined portion of the examinee's eye E in non-invasive manner by use of the optical coherence technique. The SLO optical system 300 is utilized to obtain a front image of the predetermined portion of the examinee's eye E. In the present embodiment explained below, the predetermined portion of the examinee's eye E is assumed to be a fundus area of the examinee's eye E, but it is not limited thereto and may be any predetermined portion other than the fundus (e.g., an anterior segment). The OCT optical system 200 shown in the present embodiment is a spectral domain OCT optical system, but it is not limited thereto. Other examples of the OCT optical system 200 may include other type OCT optical systems such as a time domain OCT optical system (TD-OCT) and a swept source domain OCT optical system (SS-OCT).

In the present embodiment, as shown in FIG. 1, an optical path of measurement light in the OCT optical system 200 and an optical path of a laser beam by the SLO optical system 300 are combined by an optical path combiner (a beam-combiner/beam-splitter). The present embodiment shows an example of using a dichroic mirror 40 which is one kind of the beam-combiner/beam-splitter. In the example shown in FIG. 1, the dichroic mirror 40 reflects the measurement light generated by the OCT optical system 200, while passes the laser beam generated by the SLO optical system 300, to direct the measurement light and the laser beam into a common optical path. The details of the dichroic mirror 40 and the common optical path will be described later. It may be also arranged that the dichroic mirror 40 transmits the measurement light of the OCT optical system 200 and reflects the laser beam of the SLO optical system 300.

The ophthalmic photographing apparatus 1 may also include an anterior segment observation optical system 90, an alignment mark projecting optical system 150, and others, as shown in FIG. 1. Those optical systems 90 and 150 are used for instance to align the foregoing optical systems with the examinee's eye E. For example, the anterior segment observation optical system 90 shown in FIG. 1 is an optical system to be used to obtain an observation image of a front surface of an anterior segment. This anterior segment observation optical system 90 in FIG. 1 includes an objective lens 10, a dichroic mirror 91, a lens 95, and a two-dimensional imaging element 97. As a light source of the anterior segment observation optical system 90, infrared light sources 151 mentioned later may be used. The alignment mark projecting optical system 150 is utilized to project an alignment mark. This optical system 150 in FIG. 1 includes a plurality of infrared light sources 151 arranged concentrically around the measurement optical axis L1.

<SLO Optical System>

The details of the SLO optical system 300 will be explained below. This SLO optical system 300 includes a scanning part 64 (a first optical scanner in the present embodiment) configured to scan a laser beam, which is irradiated to the Examinee's eye E, over a predetermined portion of the eye E and obtain a front image of the predetermined portion by use of the laser beam. An independent part of the SLO optical system 300 from the OCT optical system 200 is provided on a transmitting side of the dichroic mirror 40 as described above.

The SLO optical system 300 is roughly divided into a light projecting optical system 301 and a light receiving optical system 302. The light projecting optical system 301 is configured to project a laser beam from an SLO light source (a laser source) to a fundus of the examinee's eye. The light receiving optical system 302 is provided with a light receiving element 68 for receiving the light reflected by the fundus of the examinee's eye E (that is, fundus reflection light of the laser beam). The ophthalmic photographing apparatus 1 obtains a front image of the fundus of the examinee's eye based on a light receiving signal output from the light receiving element 68.

In the present embodiment, the light projecting optical system 301 includes a laser source 61, a collimator lens 65, a beam splitter 62, a focusing lens 63, a scanning part 64, the dichroic mirror 40, the dichroic mirror 91, and the objective lens 10.

In the present embodiment, the laser source 61 emits light having wavelengths in an infrared region as the laser beam. Examples of the laser source 61 may include an LED light source, an SLD light source, and others.

In the present embodiment, the focusing lens 63 serves as a diopter correcting optical system in the SLO optical system 300. Specifically, the focusing lens 63 is utilized for correcting the diopter of the SLO optical system 300. As shown in FIG. 1, the ophthalmic photographing apparatus 1 includes a drive mechanism (an actuator) 63a configured to displace the position of the focusing lens 63 in an optical axis direction. Therefore, a correction amount of the diopter by the focusing lens 63 is adjusted according to driving of the drive mechanism 63a. The focusing lens 63 is displaced so as to cancel out refraction error of the examinee's eye E to thereby perform the diopter correction in the SLO optical system 300.

The scanning part 64 is placed in an optical path of the laser beam and used to scan the laser beam on a predetermined portion (on the fundus in the present embodiment) in a transverse direction (a X-Y direction). In the present embodiment, the scanning part 64 includes a combination of two optical scanners (the first optical scanner); concretely, a resonant scanner 64a and a galvano mirror 64b (see FIG. 2). The scanning part 64 is configured to drive the two optical scanners in combination to two-dimensionally scan the laser beam from the laser source 61 over the fundus. In the present embodiment, the resonant scanner 64a is used for main scanning and the galvano mirror 64b is used for sub-scanning. In one example, the galvano mirror 64b scans the laser beam in a vertical direction, while the resonant scanner 64a scans the laser beam in a lateral (traverse) direction. The scanning part 64 is placed in a conjugate position with a pupil of the examinee's eye E. In this case, for instance, an intermediate point between the resonant scanner 64a and the galvano mirror 64b may be located in the pupil-conjugate position. In the present disclosure, the term "conjugate" is not necessarily limited to a perfect conjugate relation. In the present disclosure, the "conjugate" relation may include a positional relation displaced from the perfect conjugate relation within a permissible accuracy range as well as the perfect conjugate relation.

In the present embodiment, the light receiving optical system 302 is provided with a condensing lens 66, a confocal aperture 67 (e.g., a pinhole plate), and an SLO light receiving element 68. These components are arranged in a reflection direction of the beam splitter 62. The light receiving optical system 302 shares the components from the beam splitter 62 to the objective lens 10 with the light projecting optical system 301. The confocal aperture 67 is disposed in a position conjugate with a fundus.

Herein, a laser beam emitted from the laser source 61 enters the scanning part 64 via the collimator lens 65, the beam splitter 62, and the focusing lens 63. The reflection direction of the laser beam is then changed by driving of the resonant scanner 64a and the galvano mirror 64b. The laser beam passing through the scanning part 64 passes through the dichroic mirror 40, then through the dichroic mirror 91 and the objective lens 10, and thereby is condensed on the fundus of the examinee's eye E.

The laser beam is reflected by the fundus and travels back along the light projecting path of the SLO optical system 300 to the beam splitter 62. Specifically, the fundus reflection light of the laser beam passes through the objective lens 10, the dichroic mirror 91, the dichroic mirror 40, and the scanning part 64 and then is reflected by the beam splitter 62. Thereafter, the light falls on the light receiving element 68 via the condensing lens 66 and the confocal aperture 67. A light receiving signal from the light receiving element 68 is input to a controller (a processor) 70. Thus, the controller 70 obtains a front image of the fundus of the examinee's eye based on the light receiving signal from the light receiving element 68. This obtained front image is stored in a memory 72.

<OCT Optical System>

Next, the detailed structure of the OCT optical system 200 in the present embodiment will be explained below. The OCT optical system 200 includes a scanning part 23 (a second optical scanner in the present embodiment) configured to scan the measurement light, which is irradiated to the examinee's eye E, over a predetermined portion of the eye E and obtain a tomographic image of the predetermined portion by use of interference between the measurement light and reference light. As described above, the independent part of the OCT optical system 200 from the SLO optical system 300 is provided on a reflecting side of the dichroic mirror 40.

In the present embodiment, the OCT optical system 200 includes an OCT light source (a measurement light source)

27, a fiber coupler 26, a measurement light optical system 210, a reference optical system 220, and a spectroscopy optical system 800.

The OCT light source 27 emits low-coherent light to be used as the measurement light and the reference light in the OCT optical system 200. Examples of the OCT light source 27 may include an SLD light source and others may be used.

In the present embodiment, the fiber coupler 26 is a light splitting part for splitting the light directed from the OCT light source 27 through an optical fiber 38a serving as a light guide path into the measurement light and the reference light. The measurement light travels toward the examinee's eye E through an optical fiber 38b. The reference light travels toward a reference mirror 31 through an optical fiber 38c.

The measurement optical system 210 emits the measurement light having been split by the fiber coupler 26 toward the examinee's eye E. In the optical path of the measurement optical system 210 shown in FIG. 1, there are arranged an end portion 39b of the optical fiber 38b, a collimator lens 22, a focusing lens 24, the scanning part 23, a deflection angle enlarging lens 25, the dichroic mirror 40, the dichroic mirror 91, and the objective lens 10.

The collimator lens 22 serves to collimate the measurement light emerging from the end portion 39b.

In the present embodiment, the focusing lens 24 serves as a diopter correcting optical system in the OCT optical system 200. Specifically, the focusing lens 24 is utilized for correcting the diopter of the OCT optical system 200. As shown in FIG. 1, the ophthalmic photographing apparatus 1 includes a drive mechanism (an actuator) 24a configured to displace the position of the focusing lens 24. Therefore, a correction amount of the diopter by the focusing lens 24 is adjusted according to driving of the drive mechanism 24a. The focusing lens 24 is displaced so as to cancel out refraction error of the examinee's eye E to thereby perform the diopter correction in the OCT optical system 200.

The scanning part 23 is placed in an optical path of the measurement light beam and used to scan the measurement light beam on a predetermined portion (on the fundus in the present embodiment) in a transverse direction (the X-Y direction). In the present embodiment, the scanning part 23 includes a combination of two galvano mirrors 23a and 23b (one example of the second optical scanner) (see FIG. 2). In the present embodiment, the galvano mirrors 23a and 23b are individually driven to rotate, thereby changing the direction of the measurement light at a deflection angle according to changes in intensity of an electrical signal input to the drive mechanism 51. As the change in intensity of the signal input to the drive mechanism 51 (e.g., a difference between a maximum voltage and a minimum voltage) is larger, each galvano mirror 23a and 23b is operated at a larger deflection angle. In general, a galvano mirror is known as operating at a larger deflection angle than a resonant scanner used in the scanning part 64 of the SLO optical system 300. In the present embodiment, specifically, the scanning part 23 provides a driving allowable range with a larger scanning angle than the scanning part 64 of the SLO optical system. Further, the scanning part 23 is placed in a position conjugate with a pupil of the examinee's eye E. In this case, for example, an intermediate point between the two galvano mirrors 23a and 23b may be placed in the pupil-conjugate position. The scanning part 23 in the present embodiment is configured to arbitrarily adjust the reflection angle of measurement light by the two galvano mirrors 23a and 23b, thereby enabling to arbitrarily set a scanning direction of the measurement light to be scanned over the fundus. Accordingly, a tomographic image of any region of the fundus of the examinee's eye can be obtained. The end portion 39b of the optical fiber 38b is placed conjugate with the fundus of the examinee's eye.

The deflection angle enlarging lens 25 is placed to operate the scanning part 23 at a large deflection angle. The details of the deflection angle enlarging lens 25 will be explained later.

The measurement light emerging from the end portion 39b of the optical fiber 38b is collimated by the collimator lens 22 and then directed to the scanning part 23 through the focusing lens 24. The measurement light is thus changed in its reflecting direction by driving of the two galvano mirrors 23a and 23b. The measurement light reflected by the scanning part 23 passes through the deflection angle enlarging lens 25 and then is reflected by the dichroic mirror 40. Thereafter, this light passes through the dichroic mirror 91 and the objective lens 10 and then is condensed on the examinee's fundus. The measurement light is reflected (scattered) by the fundus and travels back along the light projecting optical path. In other words, the measurement light reflected or scattered by the fundus passes through the objective lens 10 and the dichroic mirror 91 and then is reflected by the dichroic mirror 40. This light further passes through the deflection angle enlarging lens 25, the scanning part 23, the focusing lens 24, and the collimator lens 22 and enters the end portions 39b of the optical fiber 38b. The measurement light entering the end portion 39b passes through the optical fiber 38b, the fiber coupler 26, and an optical fiber 38d and then reaches an end portion 84a of the optical fiber 38d.

The reference optical system 220 may be a Michelson optical system or Mach-Zehnder optical system. In the optical path of the reference optical system 220 shown in FIG. 1, there are arranged an end portion 39c of the optical fiber 38c which emits the reference light, a collimator lens 29, and the reference mirror 31. This reference mirror 31 is movable in an optical axis direction by a reference-mirror drive mechanism 50 in order to change an optical path length of the reference light.

The reference light emerging from the end portion 39c of the optical fiber 38c is collimated into a parallel beam by the collimator lens 29, reflected back by the reference mirror 31, then condensed by the collimator lens 29 to enter the end portion 39c of the optical fiber 38c. The reference light entering the end portion 39c passes through the optical fiber 38c and reaches the fiber coupler 26. In the present embodiment, as described above, the reference optical system 220 uses a reflection optical system, but it is not limited thereto. For example, as the optical system 220, a transmission optical system may be employed.

The reference light generated as above and the fundus reflection light by the measurement light are synthesized by the fiber coupler 26 into interference light, and then is emitted from the end portion 84a through the optical fiber 38d. The interference light thus enters the spectroscopy optical system 800 (a spectrometer part).

The spectroscopy optical system 800 is configured to disperse the interference light into frequency components to obtain an interference signal per frequency. In the present embodiment, the spectroscopy optical system 800 includes a collimator lens 80, a grating (a diffraction grating) 81, a condensing lens 82, and a light receiving element 83. As the light receiving element 83 in the present embodiment, an one-dimensional element (a line sensor) having sensitivity to infrared region is used.

Herein, the interference light emerging from the end portion 84a is collimated into a parallel beam by the collimator lens 80 and then dispersed into frequency components by the grating 81. The interference light dispersed into the frequency components passes through the condensing lens 82 and is concentrated on a light receiving surface of the light receiving element 83. Thus, spectral information on interference pattern is recorded on the light receiving element 83. When this spectral information is input to the controller 70, it is analyzed by use of Fourier transform, so that information on the examinee's eye E in a depth direction (A-scan signal) can be measured. Herein, the controller 70 obtains a tomographic image by causing the scanning part 23 to scan the measurement light over the fundus in a predetermined transverse direction. For instance, X-direction or Y-direction scanning allows obtaining a tomographic image in an X-Z plane or Y-Z plane on the Examiner's fundus. It is to be noted that in the present embodiment this method of one-dimensionally scanning on a fundus by the measurement light to obtain a tomographic image is called a B-scan. The obtained tomographic image is stored in the memory 72 connected to the controller 70. Further, when the measurement light is scanned two-dimensionally in the X-Y direction, a three-dimensional image of the Examiner's fundus can also be acquired.

<Common Optical Path of SLO Optical System and OCT Optical System>

The SLO optical system 300 and the OCT optical system 200 share the dichroic mirror 40 and the objective lens 10 as explained above. In the present embodiment, specifically, the dichroic mirror 40, the dichroic mirror 91, and the objective lens 10 form a common optical path of the OCT optical system 200 and the SLO optical system 300. The dichroic mirror 40 is an optical path combiner (also referred to as an optical path synthesizing part). To be more concrete, the light projecting optical path of the OCT optical system 200 and the light projecting optical path of the SLO optical system 300 are combined to direct the measurement light of the OCT optical system 200 and the laser beam of the SLO optical system 300 to a predetermined portion of the examinee's eye E through the common optical path. The dichroic mirror 40 reflects the measurement light (e.g., λ=about 840 nm) emitted from the OCT light source 27, while transmits the laser beam (having a wavelength different from the measurement light; e.g., λ=about 780 nm) emitted from the laser source 61. Accordingly, the dichroic mirror 40 combines the optical path of the measurement light which passes through the scanning part 23 in the OCT optical system 200 to be delivered to the examinee's eye E and the optical path of the laser beam which passes through the scanning part 64 in the SLO optical system 300 to be delivered to the examinee's eye E. Consequently, a measurement light axis L2 of the OCT optical system 200 is made coaxial with the measurement light axis L1 of the SLO optical system 300. The dichroic mirror 91 allows the wavelengths of the measurement light and the laser beam to pass through. In the present embodiment, the measurement light of the OCT optical system 200 and the laser beam of the SLO optical system 300, both having passed through the objective lens 10, pass through one point (that is, a turning point) on the measurement light axes L1 and L2 and then delivered to the predetermined portion of the examinee's eye E, even though the details will be mentioned later.

<Features>

Figure 2:
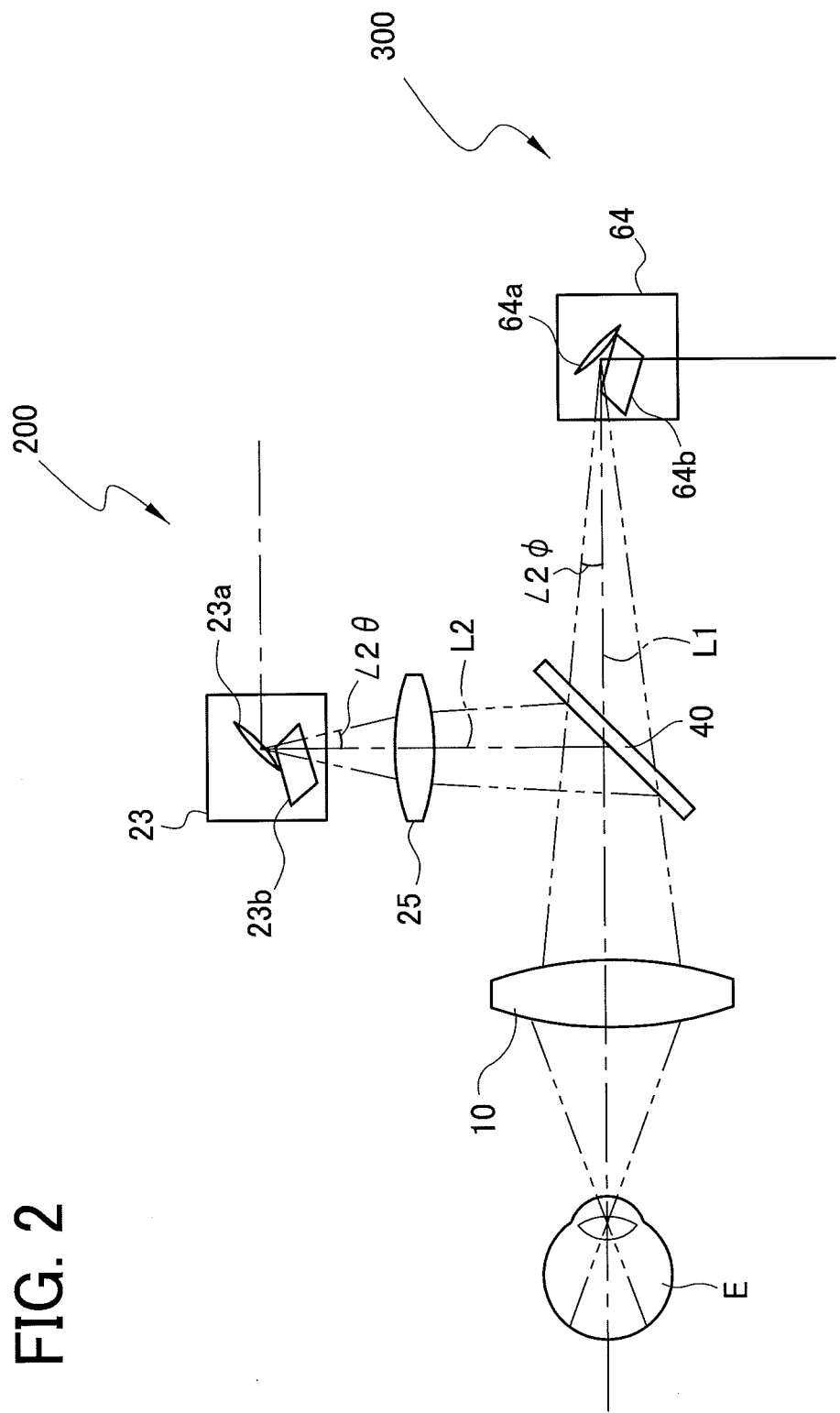
FIG. 2 is an optical path diagram showing paths of laser beam and measurement light in a characteristic part of the optical system.

Next, the features of the optical systems in the present embodiment will be explained in detail with reference to FIG. 2. FIG. 2 illustrates only the optical system components placed in the scanning part 23 and the scanning part 64 and between these scanning parts and the examinee's eye E. Other components are omitted. The dichroic mirror 91 is also omitted from the figure. In FIG. 2, a turning range of a light beam turned by operation of the optical scanner (the scanning parts 23, 64) is indicated as a region surrounded by a chain double-dashed line.

The SLO optical system 300 is configured as a non-telecentric optical system as shown in FIG. 2. In the present embodiment, the SLO optical system 300 includes no lens between the scanning part 64 and the dichroic mirror 40. Herein, the power of the objective lens 10 is determined according to the relation between a deflection angle in each of the scanning part 23 of the OCT optical system 200 and the scanning part 64 of the SLO optical system 300 and a desired scanning range. In the present embodiment, the scanning part 64 of the SLO optical system 300 uses the resonant scanner 64a. This resonant scanner 64a generally has a drivable range with a small deflection angle (a scanning angle) at a galvano mirror (e.g., the galvano mirror 23a, 23b, 64b). In the present embodiment, therefore, the objective lens 10 has a power set according to the deflection angle (angle φ) of the resonant scanner 64a. For instance, in a case where the orientation of a mirror part of the resonant scanner 64a and the galvano mirror 64b is changed at a deflection angle of about ±3.5°, a lens power of the objective lens 10 required to obtain a front image in a range of a square of 42.4°×42.4° is about 40 D. The deflection angle range of about ±3.5° may be set as a limiting deflection angle determined in view of the structure of the resonant scanner 64a. As another alternative, the deflection angle range may be a value in a range smaller than the limiting deflection angle. For example, this value may be determined in relation to a frame rate for obtaining a fundus front image.

On the other hand, in the OCT optical system 200, as in the SLO optical system 300, the optical path from the scanning part 23 toward the examinee's eye is formed by a non-telecentric optical system. The OCT optical system 200 in the present embodiment is provided, as one example of a relay lens system, with the deflection angle enlarging lens 25 (hereinafter, simply referred to as the "lens 25") in the optical path between the dichroic mirror 40 and the scanning part 23. Further, the scanning part 23 (that is, a second optical scanner) is placed on a side closer to the lens 25 than a focal point of the lens 25. Further, the scanning part 23 is placed on a side closer to the objective lens 10 than a focal point distance of the objective lens 10.

In the present embodiment, the lens 25 may function to decrease the deflection angle of the measurement light by the scanning part 23. In this case, even if the scanning part 23 is driven at a wider deflection angle than that in the scanning part 64 of the SLO optical system 300 to obtain an image, the deflection angle is narrowed by the lens 25. In other words, when the measurement light from the scanning part 23 enters the lens 25 at a position away from the center thereof, the measurement light passing through the lens 25 is refracted in a direction between an incident direction of the measurement light to the lens 25 and an optical axis direction (L2 in FIG. 1) of the lens 25 (the direction of measurement light after passing through the lens 25 is different from the incident direction of the measurement light to the lens 25 and the optical axis direction of the lens 25). Thus, the deflection angle of the optical scanner in the OCT optical system 200 can be easily ensured, thereby enabling to obtain an image at a predetermined angle of view. In the present embodiment, for instance, when the power of the lens 25 is about 20 D, each of the galvano mirrors 23a and 23b of the scanning part 23 is operated at a deflection angle θ of about ±5°, for example, a tomographic image can be obtained from a square range of about 40°×40°. Specifically, when the scanning part 23 of the OCT optical system 200 is moved at a large deflection angle with respect to the scanning part 64 of the SLO optical system 300, a tomographic image can be obtained from the angle of view nearly equal to a photographing angle of view of the SLO optical system 300.

Since the deflection angle (a deflection width) of the scanning part 23 can be largely ensured as above, it is consequently possible to suppress the influence of noise on an electric signal to drive the scanning part 23. For instance, the scanning part 23 in the present embodiment is operated at a larger deflection angle as the intensity of the electric signal (for example, a difference between a maximum voltage and a minimum voltage) input to the drive mechanism 51 is more greatly changed. In the present embodiment, since the deflection angle of the optical scanner in the OCT optical system 200 is easily obtained, therefore, an electric signal whose intensity is more largely changed can be utilized, so that the influence of noise on the electric signal to drive the scanning part is suppressed. In other words, in the electric signal, intensity changes due to noise become unnoticeable. This enables to easily perform scanning of the measurement light with high precision. Accordingly, a good tomographic image can be obtained by use of the OCT optical system 200. In the present embodiment, specifically, even if the power of the objective lens 10 is determined according to a small deflection angle of the scanning part 64 of the SLO optical system 300, the deflection angle of the scanning part 23 for obtaining a tomographic image can be made large. Consequently, a good tomographic image can be achieved.

Further, it may be arranged to narrow the deflection angle of the measurement light by the relay lens system so that the turning point of the SLO optical system and the turning point of the OCT optical system coincide with each other. In this case, the tomographic image and the front image are photographed at the same working distance. This facilitates associating the front image with the tomographic image. Since the measurement light for photographing a tomographic image and the laser beam for photographing a front image are less likely to be eclipsed by a pupil, each of the images can be obtained appropriately.

In the present embodiment, more particularly, the power of the lens 25 is set so that the relationship between the beam height and the incident angle of the light incident on the objective lens 10 is coincident, at each beam height, between the measurement light from the OCT optical system 200 and the laser beam of the SLO optical system 300. Consequently, photographing of the tomographic image using the OCT optical system 200 and photographing of the front image using the SLO optical system 300 can be performed at the same working distance. That is, the measurement light of the OCT optical system 200 having passed through the objective lens 10 and the laser beam of the SLO optical system 300 are turned about the common turning point in association with the operations of the respective scanning parts 23 and 64.

In the present embodiment, the diopter correcting optical system (the focusing lens 24 in the example shown in FIG. 1) of the OCT optical system 200 is placed on a side closer to the light source 27 than the scanning part 23 of the OCT optical system 200 is. In the present embodiment, even if the focusing lens 24 is moved to change the correction amount of the diopter, the working distance in the OCT optical system 200 is maintained constant. In the OCT optical system 200 of the present embodiment, more particularly, even if the correction amount of the diopter is changed by the diopter correcting optical system (the focusing lens 24 in the example shown in FIG. 1), the incident position and the incident angle of the measurement light to the scanning part 23 are maintained, i.e., unchanged. Even when the diopter correction is performed in the OCT optical system 200, consequently, the position of the turning point by the measurement light remains unchanged. Accordingly, the OCT optical system 200 keeps its working distance irrespective of the diopter correction amount.

Similarly, the diopter correcting optical system (the focusing lens 63 in the example shown in FIG. 1) of the SLO optical system 300 is placed on a side closer to the light source 61 than the scanning part 64 of the SLO optical system 300 is. In the present embodiment, even if the focusing lens 63 is moved to change a correction amount of the diopter, the working distance in the SLO optical system 300 is maintained constant. In the SLO optical system of the present embodiment, more particularly, even if the diopter correction amount is changed by the diopter correcting optical system (the focusing lens 63 in the example shown in FIG. 1), the incident position and the incident angle of the laser beam to the scanning part 64 are maintained, i.e., unchanged. Even when the diopter correction is performed in the SLO optical system 300, consequently, the position of the turning point by the laser beam remains unchanged. Accordingly, the SLO optical system 300 keeps its working distance irrespective of the diopter correction amount.

In the present embodiment, the working distance in each of the OCT optical system 200 and the SLO optical system 300 is constant irrespective of the diopter correction amount. Further, the working distance in the OCT optical system 200 and the working distance in the SLO optical system 300 are set equal to each other by disposing the lens 25. Therefore, irrespective of diopter error in the examinee's eye E, both photographing of a tomographic image using the OCT optical system 200 and photographing of a front image using the SLO optical system 300 can be carried out appropriately without changing the positional relationship between the examinee's eye E and the apparatus.

In the ophthalmic photographing apparatus 1 in the present embodiment, the controller 70 is a processor for performing control of each section or part and calculation. The controller (the processor) 70 is connected to a monitor 75 to control an image to be displayed on the monitor 75. The controller 70 is connected to the memory (a storage part) 72, an operating part 74 for various operations, the drive mechanism 51, the drive mechanism 52, the reference mirror drive mechanism 50, the drive mechanism 63a, the drive mechanism 24a, and others. The monitor 75 may be configured as separate monitors for alignment observation and for photographed image observation or as a single common monitor.

In the present embodiment, the drive mechanism 24a and the drive mechanism 63a are controlled to change, in a synchronization manner, the diopter correction amount in the OCT optical system 200 and the diopter correction amount in the SLO optical system 300. For instance, when the controller 70 controls the drive mechanism 24a to adjust the diopter correction amount in the OCT optical system to "+1 D", the controller 70 also simultaneously controls the drive mechanism 63a to adjust the diopter correction amount in the SLO optical system 300 to "+1 D". The term "synchronization" in the present description may include a case where the drive mechanism 24a and the drive mechanism 63a are driven at timings with a time lag therebetween and a case where both mechanisms are driven at a perfectly synchronized timing. A correction amount (a target value) in the diopter correction may be obtained for example based on an input signal from an operating part (not shown). The controller 70 may control both the drive mechanism 24a and the drive mechanism 63a to adjust the correction amounts of the diopter in the OCT optical system 200 and the SLO optical system 300 to each target value.

Modified Examples

The present disclosure, which is explained as above based on the embodiment, may be further embodied in other various forms.

For instance, the objective lens 10 in the foregoing embodiment is shown as a lens system consisting of a single lens, but may be a lens system consisting of a plurality of lenses. Further, the deflection angle enlarging lens 25 may also be configured as a lens system consisting of a plurality of lenses.

In the foregoing embodiment, two galvano mirrors are used in combination in the scanning part 23 of the OCT optical system 200 and a resonant scanner and a galvano mirror are used in combination in the scanning part 64 of the SLO optical system 300; however, the present disclosure is not limited thereto. Respective optical scanners may be another optical scanner using a reflection mirror or an acousto-optical modulator (AOM) to change a traveling (deflecting) direction of light, and others.

In the foregoing embodiment, the optical path combiner is illustrated by the dichroic mirror 40, but it is not limited thereto. The optical path combiner has only to be configured to combine the optical path of a laser beam to be directed to the examinee's eye E via the scanning part 64 of the SLO optical system 300 and the optical path of a measurement light to be directed to the examinee's eye E via the scanning part 23 of the OCT optical system 200, thereby forming a common optical path of the SLO optical system 300 and the OCT optical system 200. As alternatives to the dichroic mirror 40, for example, a half mirror or the like can be utilized as the optical path combiner.

In the present embodiment, the OCT optical system 200 and the SLO optical system 300 are explained as the diopter correcting optical systems respectively provided with the focusing lenses 24 and 63. However, each diopter correcting optical system is desired to have no influence on the direction and the position of light in entering the scanning part (optical scanner) 23 or 64 even if the diopter correction amount is changed. Thus, the diopter correcting optical systems are not necessarily limited to the above-described ones. For instance, at least one diopter correcting optical system; the OCT optical system 200 or the SLO optical system 300, may be a Badal optical system configured such that an optical path length is changed between a light source and a scanning part to adjust diopter correction amount.

What is claimed is:

1. An ophthalmic photographing apparatus comprising:
a SLO optical system including a first optical scanner for scanning a laser beam, the SLO optical system being configured to obtain a front image of an examinee's eye by the laser beam;
a OCT optical system including a second optical scanner for scanning measurement light, the OCT optical system being configured to obtain a tomographic image of the examinee's eye by use of interference between the measurement light and reference light;
an optical path combiner configured to combine an optical path of the SLO optical system and an optical path of the OCT optical system;
an objective lens system placed between the optical path combiner and the examinee's eye; and
a relay lens system placed between the second optical scanner and the optical path combiner,
wherein the second optical scanner is placed on a side closer to the relay lens system than a focal point distance of the relay lens system is.

2. The ophthalmic photographing apparatus according to claim 1, wherein the second scanner is placed on a side closer to the objective lens system than a focal point distance of the objective lens system is.

3. The ophthalmic photographing apparatus according to claim 1, wherein an optical path provided on a side closer to the examinee's eye than the first optical scanner of the SLO optical system is formed by a non-telecentric optical system.

4. The ophthalmic photographing apparatus according to claim 1, wherein the SLO optical system has no lens between the first optical scanner and the optical path combiner.

5. The ophthalmic photographing apparatus according to claim 1, wherein
the SLO optical system includes a first diopter correcting optical system in an optical path between a first light source which is a light source of the laser beam and the first optical scanner, the first diopter correcting optical system being configured to adjust a correction amount of diopter according to driving of a first actuator without changing an incident position and direction of the laser beam in entering the first optical scanner, and
the OCT optical system includes a second diopter correcting optical system in an optical path between a second light source which is a light source of the measurement light and the second optical scanner, the second diopter correcting optical system being configured to adjust a correction amount of diopter according to driving of a second actuator without changing an incident position and direction of the measurement light in entering the second optical scanner.

6. The ophthalmic photographing apparatus according to claim 5, further including a controller configured to control the first actuator and the second actuator so that the correction amount of diopter by the first diopter correcting optical system and the correction amount of diopter by the second diopter correcting optical system are changed synchronously.

7. The ophthalmic photographing apparatus according to claim 1, wherein the first optical scanner includes a resonant scanner and the second optical scanner includes a galvano mirror.

* * * * *